US011889988B2

(12) United States Patent
Taniguchi

(10) Patent No.: US 11,889,988 B2
(45) Date of Patent: Feb. 6, 2024

(54) ENDOSCOPE APPARATUS, ENDOSCOPE IMAGE PROCESSING APPARATUS, ENDOSCOPE APPARATUS ACTUATION METHOD, AND RECORDING MEDIUM

(71) Applicant: OLYMPUS CORPORATION, Tokyo (JP)

(72) Inventor: Hiroki Taniguchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 71 days.

(21) Appl. No.: 17/465,140

(22) Filed: Sep. 2, 2021

(65) Prior Publication Data

US 2021/0400181 A1    Dec. 23, 2021

Related U.S. Application Data

(63) Continuation of application No. PCT/JP2019/009366, filed on Mar. 8, 2019.

(51) Int. Cl.
*A61B 1/06* (2006.01)
*G06T 7/90* (2017.01)
(Continued)

(52) U.S. Cl.
CPC ........ *A61B 1/0638* (2013.01); *A61B 1/00009* (2013.01); *G06T 7/90* (2017.01);
(Continued)

(58) Field of Classification Search
CPC .............................. A61B 1/0638; A61B 1/055
See application file for complete search history.

(56) References Cited

U.S. PATENT DOCUMENTS 6,026,319 A * 2/2000 Hayashi ............... A61B 5/0071
600/478
2008/0246419 A1   10/2008 Deurenberg
(Continued)

FOREIGN PATENT DOCUMENTS

EP    2 702 927 A1   3/2014
EP    2 850 994 A1   3/2015
(Continued)

OTHER PUBLICATIONS

WIPO, International Preliminary Report on Patentability for PCT/JP2019/009366 (dated Aug. 2021) (Year: 2021).*
(Continued)

*Primary Examiner* — David N Werner
(74) *Attorney, Agent, or Firm* — Scully, Scott, Murpy & Presser, P.C.

(57) ABSTRACT

An endoscope apparatus includes: a light source apparatus; an image pickup apparatus configured to pick up an image of an object including a region containing hemoglobin irradiated with illumination light and output an image-pickup signal; and a processor. The processor performs predetermined image processing on at least one of a first image and a second image and outputs the one image, the first image being obtained by performing image pickup of the object irradiated with the first light, the second image being obtained by performing image pickup of the object irradiated with the second light, and generates an observation image by using the first and second images obtained as a processing result of the predetermined image processing.

19 Claims, 3 Drawing Sheets

(51) Int. Cl.
*H04N 9/68* (2023.01)
*H04N 9/77* (2006.01)
*A61B 1/00* (2006.01)
*H04N 23/56* (2023.01)
*H04N 23/71* (2023.01)
*H04N 23/72* (2023.01)
*H04N 25/11* (2023.01)
*A61B 1/05* (2006.01)
*A61B 1/07* (2006.01)
*H04N 23/50* (2023.01)

(52) U.S. Cl.
CPC ............... *H04N 9/68* (2013.01); *H04N 9/77* (2013.01); *H04N 23/56* (2023.01); *H04N 23/71* (2023.01); *H04N 23/72* (2023.01); *H04N 25/11* (2023.01); *A61B 1/05* (2013.01); *A61B 1/0669* (2013.01); *A61B 1/0684* (2013.01); *A61B 1/07* (2013.01); *G06T 2207/10024* (2013.01); *G06T 2207/10068* (2013.01); *H04N 23/555* (2023.01)

(56) References Cited

U.S. PATENT DOCUMENTS

| | | |
|---|---|---|
| 2013/0265401 A1 | 10/2013 | Igarashi et al. |
| 2015/0087903 A1 | 3/2015 | Kuramoto |
| 2017/0027428 A1 | 2/2017 | Igarashi |
| 2018/0289240 A1 | 10/2018 | Aoyama |
| 2019/0053696 A1 | 2/2019 | Igarashi et al. |
| 2019/0159687 A1* | 5/2019 | Kubo .................... A61B 1/045 |

FOREIGN PATENT DOCUMENTS

| | | |
|---|---|---|
| EP | 3 114 985 A1 | 1/2017 |
| JP | 2007-202942 A | 8/2007 |
| JP | 2009-514206 A | 4/2009 |
| JP | 2015-061569 A | 4/2015 |
| JP | 5974204 B1 | 8/2016 |
| JP | 2017/113185 A | 6/2017 |
| JP | 2019-041946 A | 3/2019 |
| WO | 2007/049180 A1 | 5/2007 |
| WO | 2013/145410 A1 | 10/2013 |
| WO | 2016/147435 A1 | 9/2016 |
| WO | 2017/110334 A1 | 6/2017 |
| WO | 2018/008185 A1 | 1/2018 |
| WO | 2018/230396 A1 | 12/2018 |
| WO | 2019/017051 A1 | 1/2019 |
| WO | 2019/053804 A1 | 3/2019 |

OTHER PUBLICATIONS

International Search Report dated May 28, 2019 received in PCT/JP2019/009366.

* cited by examiner

| CURRENT VALUE CV (AMPERES) | SIGNAL OUTPUT RATIO SR |
|---|---|
| CVA | SRA |
| CVB | SRB |
| CVC | SRC |
| ⋮ | ⋮ |
| CVM | 1.0 |

TD

ENDOSCOPE APPARATUS, ENDOSCOPE IMAGE PROCESSING APPARATUS, ENDOSCOPE APPARATUS ACTUATION METHOD, AND RECORDING MEDIUM

CROSS REFERENCE TO RELATED APPLICATION

This application is a continuation application of PCT/JP2019/009366 filed on Mar. 8, 2019, the entire contents of which are incorporated herein by this reference.

BACKGROUND OF THE INVENTION

1. Field of the Invention

The present invention relates to an endoscope apparatus, an endoscope image processing apparatus, an endoscope apparatus actuation method, and a recording medium.

2. Description of the Related Art

In an observation method conventionally disclosed for endoscope observation in a medical field, a living body tissue is irradiated with narrow-band light having a central wavelength (wavelength band) set in accordance with a light absorption characteristic of hemoglobin so that a blood vessel existing at a desired depth of the living body tissue is visualized.

Specifically, for example, Japanese Patent Publication No. 5974204 discloses a configuration in which a living-body mucous membrane is irradiated with narrow-hand light near 600 nm, which is light relatively easily absorbed by hemoglobin, and light near 630 nm which is light relatively hardly absorbed by hemoglobin, to visualize both a blood vessel existing at a deep part of the living-body mucous membrane and an outline of a background part extending from a surface layer of the living-body mucous membrane to the deep part. In addition, Japanese Patent Publication No. 5974204 discloses a configuration of a light source apparatus including an LED configured to generate narrow-band light near 600 nm and an LED configured to generate light near 630 nm.

In the above-described observation method, a semiconductor light source such as an LED and an LD (laser diode) is typically used as a light source configured to generate narrow-band light. However, when such a semiconductor light source is used in the above-described observation method, a situation can occur that a displayed image has a color tone different from an original color tone due to shift of a central wavelength (wavelength band) of narrow-band light emitted from the semiconductor light source from an original central wavelength (wavelength band).

SUMMARY OF THE INVENTION

An endoscope apparatus according to an aspect of the present invention includes: a light source apparatus configured to sequentially or simultaneously generate first light and second light as illumination light, the first light being in a predetermined wavelength range that belongs to a red color gamut, the second light being out of the predetermined wavelength range and having a shorter wavelength than the first light; an image pickup apparatus configured to perform image pickup of return light from an object and output an image-pickup signal; and a processor. The processor is configured to: perform predetermined image processing on at least one of a first image and a second image and generate and output an observation image to a display apparatus, the first image being obtained by return light from the first light, the second image being obtained by return light from the second light; and acquire, based on a detection result of a predetermined parameter indicating a present operation state of a predetermined light source corresponding to a generation source of the first light in the light source apparatus, signal intensity information of an image-pickup signal outputted from the image pickup apparatus in accordance with irradiation of the object with the first light, and then perform, based on the signal intensity information, control for maintaining, at a constant ratio, a brightness ratio of the first and second images. The processor is further configured to: acquire the signal intensity information calculated as a ratio of signal intensity of the image-pickup signal outputted from the image pickup apparatus when the object is irradiated with the first light having a central wavelength different from a predetermined central wavelength, with respect to reference signal intensity of the image-pickup signal outputted from the image pickup apparatus when the object is irradiated with the first light having the predetermined central wavelength; perform, based on the acquired signal intensity information, color adjustment processing for adjusting brightness of the first image or the second image; and perform color correction processing for decreasing saturation of a region not containing hemoglobin in the first or second image based on the acquired signal intensity information and two color differences calculated by using the first or second image obtained as a processing result of the color adjustment processing.

An endoscope image processing apparatus according to an aspect of the present invention is an endoscope image processing apparatus used in an endoscope apparatus including a light source apparatus and an image pickup apparatus, the light source apparatus being configured to sequentially or simultaneously generate first light and second light as illumination light, the first light being in a predetermined wavelength range that belongs to a red color gamut, the second light being out of the predetermined wavelength range and having a shorter wavelength than the first light, the image pickup apparatus being configured to perform image pickup of return light from an object and output an image-pickup signal, the endoscope image processing apparatus including a processor. The processor is configured to: perform predetermined image processing on at least one of a first image and a second image and generate and output an observation image to a display apparatus, the first image being obtained by return light from the first light, the second image being obtained by return light from the second light; and acquire, based on a detection result of a predetermined parameter indicating a present operation state of a predetermined light source corresponding to a generation source of the first light in the light source apparatus, signal intensity information of an image-pickup signal outputted from the image pickup apparatus in accordance with irradiation of the object with the first light, and then perform, based on the signal intensity information, control for maintaining, at a constant ratio, a brightness ratio of the first and second images. The processor is further configured to: acquire the signal intensity information calculated as a ratio of signal intensity of the image-pickup signal outputted from the image pickup apparatus when the object is irradiated with the first light having a central wavelength different from a predetermined central wavelength, with respect to reference signal intensity of the image-pickup signal outputted from the image pickup apparatus when the object is irradiated with the first light having the predetermined central wavelength; perform, based on the acquired signal intensity information, color adjustment processing for adjusting brightness of the first image or the second image; and perform color correction processing for decreasing saturation of a region not containing hemoglobin in the first or second image based on the acquired signal intensity information and two color differences calculated by using the first or second image obtained as a processing result of the color adjustment processing.

An endoscope apparatus actuation method according to an aspect of the present invention includes: sequentially or simultaneously generating, by a light source apparatus, first light and second light as illumination light, the first light being in a predetermined wavelength range that belongs to a red color gamut, the second light being out of the predetermined wavelength range and having a shorter wavelength than first light; performing, by an image pickup apparatus, image pickup of return light from an object, and outputting an image-pickup signal; performing predetermined image processing on at least one of a first image and a second image and generating and outputting an observation image to a display apparatus, the first image being obtained by return light from the first light, the second image being obtained by return light from the second light; acquiring, based on a detection result of a predetermined parameter indicating a present operation state of a predetermined light source corresponding to a generation source of the first light in the light source apparatus, signal intensity information of an image-pickup signal outputted from the image pickup apparatus in accordance with irradiation of the object with the first light; performing, by the control unit, based on the signal intensity information, control for maintaining, at a constant ratio, a brightness ratio of the first and second images; acquiring the signal intensity information calculated as a ratio of signal intensity of the image-pickup signal outputted from the image pickup apparatus when the object is irradiated with the first light having a central wavelength different from a predetermined central wavelength, with respect to the reference signal intensity of the image-pickup signal outputted from the image pickup apparatus when the object is irradiated with the first light having the predetermined central wavelength; performing, based on the acquired signal intensity information, color adjustment processing for adjusting brightness of the first image or the second image; and performing color correction processing for decreasing saturation of a region not containing hemoglobin in the first or second image based on the acquired signal intensity information and two color differences calculated by using the first or second image obtained as a processing result of the color adjustment processing.

A recording medium according to an aspect of the present invention is a non-transitory computer-readable recording medium storing a program used in an endoscope apparatus including a light source apparatus, an image pickup apparatus, and a processor, the light source apparatus being configured to sequentially or simultaneously generate first light and second light as illumination light, the first light being in a predetermined wavelength range that belongs to a red color gamut, the second light being out of the predetermined wavelength range and having a shorter wavelength than the first light, the image pickup apparatus being configured to perform image pickup of return light from an object and output an image-pickup signal, the program being configured to cause a computer to execute processing including: performing predetermined image processing on at least one of a first image and a second image and generate and output an observation image to a display apparatus, the first image being obtained by return light from the first light, the second image being obtained by return light from the second light; acquiring, based on a detection result of a predetermined parameter indicating a present operation state of a predetermined light source corresponding to a generation source of the first light in the light source apparatus, signal intensity information of an image-pickup signal outputted from the image pickup apparatus in accordance with irradiation of the object with the first light; performing, based on the signal intensity information, control for maintaining, at a constant ratio, a brightness ratio of the first and second images; acquiring the signal intensity information calculated as a ratio of signal intensity of the image-pickup signal outputted from the image pickup apparatus when the object is irradiated with the first light having a central wavelength different from a predetermined central wavelength, with respect to the reference signal intensity of the image-pickup signal outputted from the image pickup apparatus when the object is irradiated with the first light having the predetermined central wavelength; performing, based on the acquired signal intensity information, color adjustment processing for adjusting brightness of the first image or the second image; and performing color correction processing for decreasing saturation of a region not containing hemoglobin in the first or second image based on the acquired signal intensity information and two color differences calculated by using the first or second image obtained as a processing result of the color adjustment processing.

DETAILED DESCRIPTION OF THE PREFERRED EMBODIMENT

An embodiment of the present invention will be described below with reference to the accompanying drawings.

Figure 1:
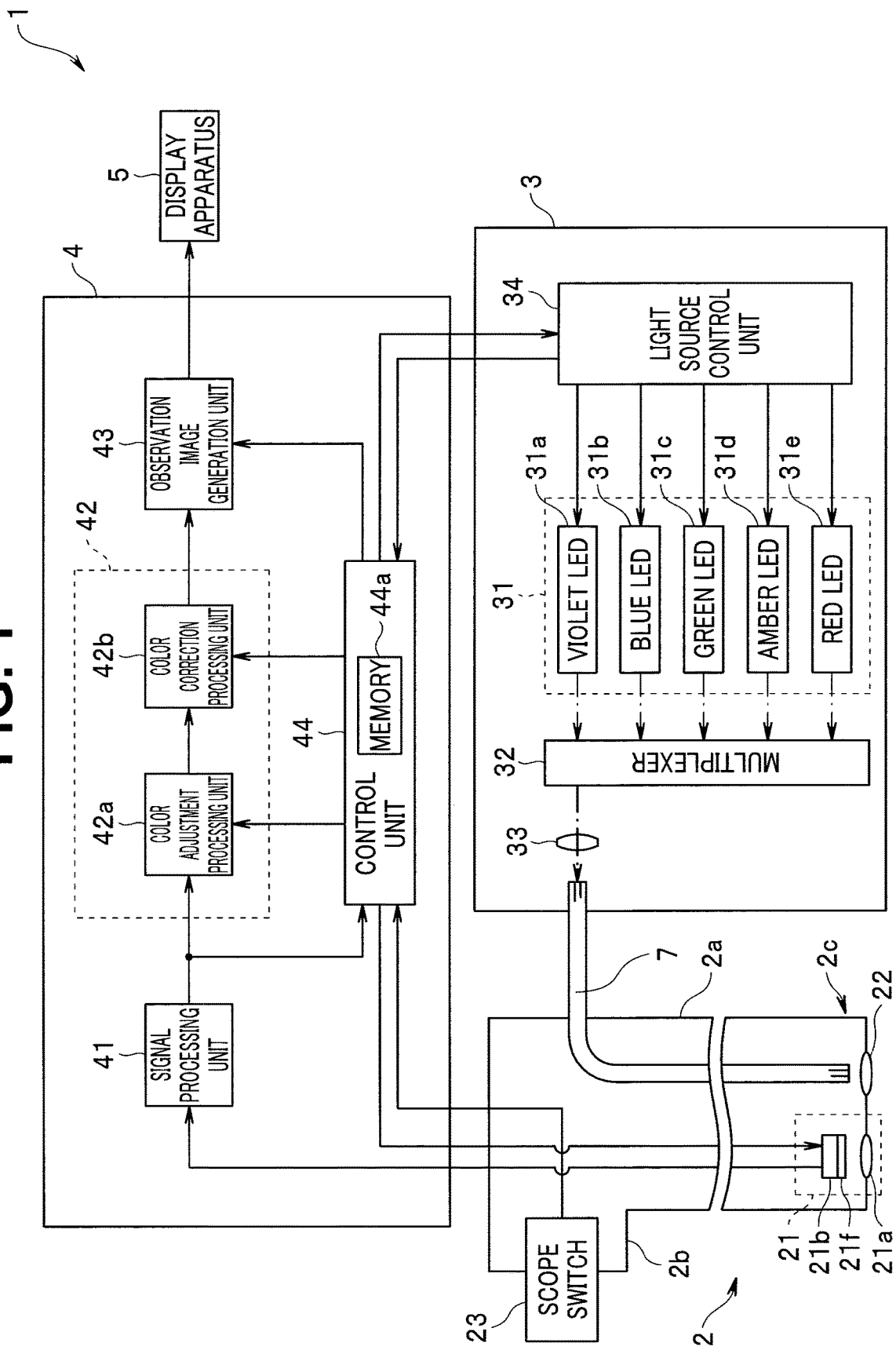
FIG. 1 is a diagram illustrating a configuration of a main part of an endoscope apparatus according to an embodiment.

As illustrated in FIG. 1, an endoscope apparatus 1 includes an endoscope 2 that can be inserted into a subject and is configured to pick up an image of an object such as a living body tissue existing in the subject and output an image-pickup signal, a light source apparatus 3 configured to supply illumination light used to observe the object through a light guide 7 inserted and disposed inside the endoscope 2, a processor 4 configured to generate and output an observation image or the like in accordance with the image-pickup signal outputted from the endoscope 2, and a display apparatus 5 configured to display the observation image outputted from the processor 4 onto a screen. FIG. 1 is a diagram illustrating a configuration of a main part of the endoscope apparatus according to the embodiment.

The endoscope 2 includes an insertion portion 2a formed in an elongated shape with which the insertion portion 2a can be inserted into the subject, and an operation portion 2b provided on a proximal end side of the insertion portion 2a. The endoscope 2 is configured to be detachably connected with the processor 4 through, for example, a universal cable (not illustrated) in which a signal line used to transmit various kinds of signals including an image-pickup signal outputted from an image pickup unit 21 (to be described later) is provided. The endoscope 2 is also configured to be detachably connected with the light source apparatus 3 through a light guide cable (not illustrated) in which at least part of the light guide 7 is provided.

The image pickup unit 21 for picking up an image of an object such as a living body tissue in the subject, an emission end part of the light guide 7, and an illumination optical system 22 through which illumination light transmitted through the light guide 7 is incident on the object are provided at a distal end portion 2c of the insertion portion 2a.

The image pickup unit 21 is an image pickup apparatus configured to perform image pickup of return light from an object irradiated with illumination light from the illumination optical system 22 and output an image-pickup signal. Specifically, the image pickup unit 21 includes an objective optical system 21a configured to form an image of return light emitted from an object irradiated with illumination light from the illumination optical system 22, and an image pickup device 21b in which a plurality of pixels for receiving the return light and picking up an image are disposed in a matrix of rows and columns in accordance with an image forming position of the objective optical system 21a.

The image pickup device 21b includes an image sensor such as a CCD sensor or a CMOS sensor. The image pickup device 21b is configured as a color image pickup device in which a color filter 21f of a primary color Bayer array is attached on an image pickup surface formed by a plurality of pixels arranged for receiving return light emitted from an object and picking up an image. The image pickup device 21b performs operation in accordance with a control signal outputted from the processor 4. The image pickup device 21b is configured to generate an image-pickup signal by performing image pickup of return light imaged by the objective optical system 21a and output the generated image-pickup signal to the processor 4. Note that, in the present embodiment, the color filter 21f may be configured by, for example, an array other than a Bayer array. In the present embodiment, the color filter 21f may be configured as a filter having a complementary color.

Specifically, the color filter 21f provided on the image pickup surface of the image pickup device 21b includes a blue color filter having an optical property that allows transmission of V light and B light to be described later, a green color filter having an optical property that allows transmission of G light to be described later, and a red color filter having an optical property that allows transmission of A light and R light to be described later. The image pickup device 21b is configured to output, to the processor 4, an image-pickup signal generated by performing image pickup of light that is included in return light emitted from an object and has passed through the blue color filter in the color filter 21f, an image-pickup signal generated by performing image pickup of light that is included in the return light and has passed through the green color filter in the color filter 21f, and an image-pickup signal generated by performing image pickup of light that is included in the return light and has passed through the red color filter in the color filter 21f.

The operation portion 2b has a shape with which the operation portion 2b can be grasped and operated by a user. The operation portion 2b is provided with a scope switch 23 including one or more switches through which an instruction in accordance with an input operation by the user can be performed to the processor 4. Specifically, the scope switch 23 includes, for example, an observation mode switching switch (not illustrated) through which an instruction for setting (switching) an observation mode of the endoscope apparatus 1 to one of a white light observation mode and a special light observation mode can be performed in accordance with an operation by the user.

The light source apparatus 3 includes a light emission unit 31, a multiplexer 32, a light condensation lens 33, and a light source control unit 34.

The light emission unit 31 includes a violet LED 31a, a blue LED 31b, a green LED 31c, an amber LED 31d, and a red LED 31e. In other words, the light emission unit 31 includes a plurality of semiconductor light sources. Note that, for example, laser diodes (LDs) may be provided in place of LEDs in the light emission unit 31.

Figure 2:
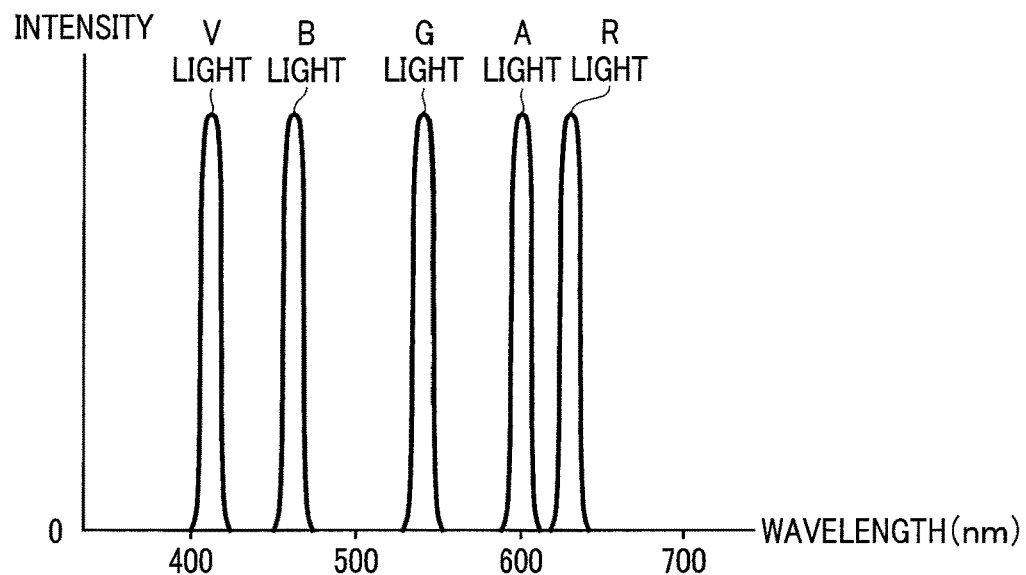
FIG. 2 is a diagram illustrating an example of a wavelength band of light emitted from each LED provided in a light source apparatus according to the embodiment.
Figure 3:
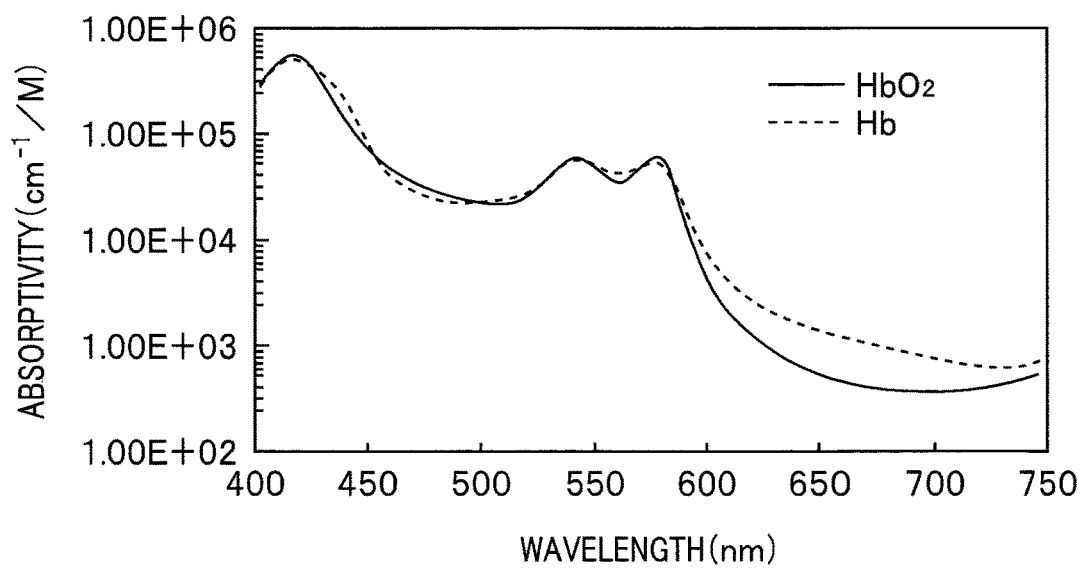
FIG. 3 is a diagram illustrating light absorption characteristics of oxidized hemoglobin and reduced hemoglobin.

The violet LED 31a is configured to generate violet narrow-band light (hereinafter, referred to as V light). Specifically, the violet LED 31a is configured to generate, as V light, for example, light having a central wavelength set to be near 410 nm and having a bandwidth set to be 20 nm approximately as illustrated in FIG. 2. The violet LED 31a is configured to or not to perform light emission in accordance with control by the light source control unit 34. The violet LED 31a is configured to generate V light having a light emission quantity in accordance with control by the light source control unit 34. FIG. 2 is a diagram illustrating an example of a wavelength band of light emitted from each LED provided in the light source apparatus according to the embodiment. FIG. 3 is a diagram illustrating light absorption characteristics of oxidized hemoglobin and reduced hemoglobin.

The blue LED 31b is configured to generate blue narrow-band light (hereinafter, referred to as B light). Specifically, the blue LED 31b is configured to generate, as B light, for example, light having a central wavelength set to be near 460 nm and having a bandwidth set to be 20 nm approximately as illustrated in FIG. 2. In other words, B light emitted from the blue LED 31b has intensity in a blue color gamut on a long wavelength side of V light. The blue LED 31b is configured to or not to perform light emission in accordance with control by the light source control unit 34. The blue LED 31b is configured to generate B light having a light emission quantity in accordance with control by the light source control unit 34.

The green LED 31c is configured to generate green narrow-band light (hereinafter, referred to as G light). Specifically, the green LED 31c is configured to generate, as G light, for example, light having a central wavelength set to be near 540 nm and having a bandwidth set to be 20 nm approximately as illustrated in FIG. 2. In other words, G light emitted from the green LED 31c has intensity in a green color gamut on the long wavelength side of V light (and B light). The green LED 31c is configured to or not to perform light emission in accordance with control by the light source control unit 34. The green LED 31c is configured to generate G light having a light emission quantity in accordance with control by the light source control unit 34.

The amber LED 31d is configured to generate amber narrow-band light (hereinafter, referred to as A light). Specifically, the amber LED 31d is configured to generate, as A light, for example, light having a central wavelength set to be near 600 nm and having a bandwidth set to be 20 nm approximately as illustrated in FIG. 2. In other words, A light emitted from the amber LED 31*d* has intensity in a predetermined wavelength range that corresponds to a section from a wavelength band including a local maximum value to a wavelength band including a local minimum value in a light absorption characteristic of hemoglobin and belongs to a red color gamut, which is exemplarily illustrated in FIG. 3. The amber LED 31*d* is configured to or not to perform light emission in accordance with control by the light source control unit 34. The amber LED 31*d* is configured to generate A light having a light emission quantity in accordance with control by the light source control unit 34.

The red LED 31*e* is configured to generate red narrow-band light (hereinafter, referred to as R light). Specifically, the red LED 31*e* is configured to generate, as R light, for example, light having a central wavelength set to be near 630 nm and having a bandwidth se to be 20 nm approximately as illustrated in FIG. 2. In other words, R light emitted from the red LED 31*e* has intensity in a red color gamut on the long wavelength side of A light. The red LED 31*e* is configured to or not to perform light emission in accordance with control by the light source control unit 34. The red LED 31*e* is configured to generate R light having a light emission quantity in accordance with control by the light source control unit 34.

The multiplexer 32 is configured to be able to multiplex light emitted from the light emission unit 31 and cause the multiplexed light to be incident on the light condensation lens 33.

The light condensation lens 33 is configured to condense the light incident through the multiplexer 32 and emit the condensed light to the light guide 7.

The light source control unit 34 includes, for example, a drive circuit and a control circuit. The light source control unit 34 is configured to be able to supply current needed to operate each LED of the light emission unit 31. The light source control unit 34 is configured to operate each LED of the light emission unit 31 in accordance with a control signal outputted from the processor 4.

Note that, in the present embodiment, the wavelength band of light emitted from each LED of the light emission unit 31 is set not to mutually overlap. According to the present embodiment, the central wavelength of A light can be set to be a wavelength belonging to a range of 585 nm to 615 nm inclusive as long as the wavelength band of A light and the wavelength band of R light do not mutually overlap. In addition, according to the present embodiment, the central wavelength of G light can be set to be any wavelength shorter than 585 nm as long as the wavelength band of G light and the wavelength band of A light do not mutually overlap. In addition, according to the present embodiment, the central wavelength of V light can be set to be any wavelength equal to or longer than 400 nm as long as the wavelength band of V light and the wavelength band of B light do not mutually overlap. In the present embodiment, V light. B light, G light, and R light do not necessarily need to be narrow-band light. In the present embodiment, narrow-band light only needs to be, for example, light having a wavelength band narrower than each color region when a wavelength band of visible light is divided into three primary colors of R (red), (3 (green), and B (blue) and having a bandwidth of several tens nm approximately.

Specifically, the light emission unit 31 of the present embodiment is configured to be able to sequentially or simultaneously generate narrow-band light NX and light NY as illumination light in accordance with control by the light source control unit 34, the narrow-band light NX having intensity in a predetermined wavelength range that corresponds to a section from a wavelength band including a local maximum value to a wavelength band including a local minimum value in a light absorption characteristic of hemoglobin and belongs to a red color gamut, the light NY having intensity out of the predetermined wavelength range and on a short wavelength side of the narrow-band light NX. In the present embodiment, a wavelength band of the narrow-band light NX is set not to overlap a wavelength band of the light NY, and a central wavelength of the narrow-band light NX is set to be a wavelength belonging to a range of 585 nm to 615 nm inclusive. In the present embodiment, the wavelength band of the light NY is set not to overlap the wavelength band of the narrow-band light NX, and a central wavelength of the light NY is set to be a wavelength belonging to a range equal to or longer than 400 nm and shorter than 585 nm.

The processor 4 has functions of an endoscope image processing apparatus. The processor 4 includes a signal processing unit 41, an image processing unit 42, an observation image generation unit 43, and a control unit 44.

The signal processing unit 41 includes, for example, a signal processing circuit. The signal processing unit 41 is configured to generate image data by performing predetermined signal processing such as A/D conversion on the image-pickup signal outputted from the endoscope 2 and output the generated image data to the image processing unit 42 and the control unit 44.

The image processing unit 42 includes, for example, an image processing circuit. The image processing unit 42 is configured to perform predetermined image processing on image data outputted from the signal processing unit 41 and output the image data to the observation image generation unit 43. The image processing unit 42 includes, for example, a color adjustment processing unit 42*a* and a color correction processing unit 42*b*.

The color adjustment processing unit 42*a* is configured to perform, in accordance with a control signal outputted from the control unit 44, color adjustment processing on the image data outputted through the signal processing unit 41, and output the image data subjected to the color adjustment processing to the color correction processing unit 42*b*. Note that a specific example of the color adjustment processing performed at the color adjustment processing unit 42*a* will be described later.

The color correction processing unit 42*b* is configured to perform, in accordance with a control signal outputted from the control unit 44, color correction processing on the image data outputted through the color adjustment processing unit 42*a*, and output the image data subjected to the color correction processing to the observation image generation unit 43. Note that a specific example of the color correction processing performed at the color correction processing unit 42*b* will be described later.

The observation image generation unit 43 includes, for example, an image generation circuit. The observation image generation unit 43 is configured to generate, in accordance with a control signal outputted from the control unit 44, an observation image by allocating the image data of each color component, which is outputted through the image processing unit 42, to a R (red) channel, a G (green) channel, and a B (blue) channel of the display apparatus 5, and output the generated observation image to the display apparatus 5.

The control unit 44 includes, for example, a control circuit. The control unit 44 is configured to generate and output, based on an instruction provided through the observation mode switching switch of the scope switch 23, a control signal for performing an operation in accordance with the observation mode of the endoscope apparatus 1. The control unit 44 is also configured to generate and output a control signal for controlling operation of the image pickup device 21b. The control unit 44 is also configured to generate and output a control signal for controlling operation of each LED of the light emission unit 31 through the light source control unit 34.

The control unit 44 includes a memory 44a in which one or more pieces of table data (to be described later) are stored. The control unit 44 is configured to perform, based on the image data outputted from the signal processing unit 41, brightness detection processing for detecting present brightness in an observation mode set through the scope switch 23. The control unit 44 is also configured to generate a control signal for performing light modulation operation through which the present brightness obtained as a processing result of the above-described brightness detection processing becomes closer to a predetermined brightness target value, and output the generated control signal to the light source control unit 34. The control unit 44 is also configured to be able to detect a present value of a magnitude of current (hereinafter, also referred to as a present value of current) supplied from the light source control unit 34 to each LED of the light emission unit 31 along with the above-described light modulation operation. The control unit 44 is also configured to, when the observation mode of the endoscope apparatus 1 is set to the special light observation mode, acquire, by referring to table data read from the memory 44a, a signal output ratio (to be described later) corresponding to a detection result of the present value of current supplied from the light source control unit 34 to a predetermined LED of the light emission unit 31 along with the above-described light modulation operation, and output a control signal including the acquired signal output ratio to the color adjustment processing unit 42a and the color correction processing unit 42b.

Note that, in the present embodiment, for example, a lag-lead filter having a time constant for defining an operation interval of the above-described light modulation operation is desirably provided in the light source control unit 34 to avoid occurrence of hunting along with the light modulation operation.

In the present embodiment, for example, each component of the processor 4 may be configured as an individual electronic circuit or may be configured as a circuit block in an integrated circuit such as a field programmable gate array (FPGA). In the present embodiment, for example, the processor 4 may include one or more CPUs. In the present embodiment, for example, the control unit 44 may read and execute a program stored in the memory 44a to cause a computer to perform operation, processing, and the like in accordance with a function of each component of the processor 4.

The display apparatus 5 includes, for example, a liquid crystal display (LCD) and is configured to be able to display an observation image outputted from the processor 4 and the like.

Subsequently, effects of the present embodiment will be described below.

A user such as an operator, for example, connects components of the endoscope apparatus 1 and powers on the endoscope apparatus 1, and then operates the observation mode switching switch of the scope switch 23 to provide an instruction for setting the observation mode of the endoscope apparatus 1 to the white light observation mode.

The following describes a specific example of operation of each component when the observation mode of the endoscope apparatus 1 is set to the white light observation mode.

When having detected that an instruction for setting the observation mode of the endoscope apparatus 1 to the white light observation mode is provided, the control unit 44 generates a control signal for simultaneously emitting B light, G light, and R light from the light source apparatus 3 and outputs the generated control signal to the light source control unit 34. In addition, the control unit 44 having detected that the instruction for setting the observation mode of the endoscope apparatus 1 to the white light observation mode is provided generates a control signal for performing operation in accordance with the white light observation mode and outputs the generated control signal to the color adjustment processing unit 42a, the color correction processing unit 42b, and the observation image generation unit 43.

In the white light observation mode, the light source control unit 34 controls the light emission unit 31, for example, not to emit light from the violet LED 31a and the amber LED 31d and to simultaneously emit light from the blue LED 31b, the green LED 31c, and the red LED 31e in accordance with the control signal outputted from the control unit 44. Then, in accordance with such operation of the light source control unit 34, an object is irradiated with illumination light including B light, G light, and R light, and an image-pickup signal BS generated through image pickup of the B light included in return light of the illumination light, an image-pickup signal GS generated through image pickup of the G light included in the return light, and an image-pickup signal RS generated through image pickup of the R light included in the return light are outputted from the image pickup device 21b to the signal processing unit 41.

The signal processing unit 41 performs predetermined signal processing on the image-pickup signals BS, GS, and RS outputted from the image pickup device 21b to generate image data PB that is image data of a blue color component in accordance with signal intensity of the image-pickup signal BS, image data PG that is image data of a green color component in accordance with signal intensity of the image-pickup signal GS, and image data PR that is image data of a red color component in accordance with signal intensity of the image-pickup signal RS, and then outputs the generated image data PB, PG, and PR to the image processing unit 42 and the control unit 44.

The control unit 44 performs brightness detection processing for detecting present brightness WCB in the white light observation mode based on the image data of each color component outputted from the signal processing unit 41.

Specifically, in the above-described brightness detection processing, for example, the control unit 44 calculates an average value of pixel values of pixels included in the image data PB, PG, and PR outputted from the signal processing unit 41, and performs processing for detecting the calculated average value as the present brightness WCB in the white light observation mode. Note that, in the above-described brightness detection processing, for example, the control unit 44 may perform processing for detecting, as the present brightness WCB in the white light observation mode, one of a weighted average value of the pixel values of pixels included in the image data PB, PG, and PR outputted from the signal processing unit 41, or an average value of the pixel values of pixels included in the image data of a predetermined color component outputted from the signal processing unit 41.

When performing the above-described brightness detection processing, the control unit 44 may perform the processing for an entire range of the image data outputted from the signal processing unit 41 or only for a partial region included in the image data outputted from the signal processing unit 41.

The control unit 44 generates a control signal for performing light modulation operation through which the present brightness WCB obtained as a processing result of the above-described brightness detection processing becomes closer to a brightness target value WTB in the white light observation mode, and outputs the generated control signal to the light source control unit 34.

Specifically, the control unit 44 generates a control signal for performing, for example, light modulation operation through which a ratio (WCB/WTB) of the present brightness WCB relative to the brightness target value WTB becomes closer to one, and outputs the generated control signal to the light source control unit 34.

Through the above-described operation of the control unit 44, B light, G light, and R light having light quantities suitable for white light observation are supplied as illumination light from the light source apparatus 3 to the endoscope 2.

In the white light observation mode, the color adjustment processing unit 42*a* performs, for example, white balance adjustment processing on the image data of each color component outputted through the signal processing unit 41 in accordance with the control signal outputted from the control unit 44, and outputs the image data of each color component subjected to the white balance adjustment processing to the color correction processing unit 42*b*.

In the white light observation mode, the color correction processing unit 42*b* performs, for example, gamma correction processing on the image data of each color component outputted through the color adjustment processing unit 42*a* in accordance with the control signal outputted from the control unit 44, and outputs the image data of each color component subjected to the gamma correction processing to the observation image generation unit 43.

In the white light observation mode, the observation image generation unit 43 generates, in accordance with the control signal outputted from the control unit 44, a white light observation image by, for example, allocating the image data PB outputted through the color correction processing unit 42*b* to the B channel of the display apparatus 5, allocating the image data PG outputted through the color correction processing unit 42*b* to the G channel of the display apparatus 5 and allocating the image data PR outputted through the color correction processing unit 42*b* to the R channel of the display apparatus 5, and outputs the generated white light observation image to the display apparatus 5.

Through the above-described operation of each component, a white light observation image having a color tone substantially the same as a color tone when, for example, an object such as a living body tissue is viewed with bare eye is displayed on the display apparatus 5 when the observation mode of the endoscope apparatus 1 is set to the white light observation mode.

While checking the white light observation image displayed on the display apparatus 5 in a state in which the observation mode of the endoscope apparatus 1 is set to the white light observation mode, the user inserts the insertion portion 2*a* into a body cavity of an examinee and disposes the distal end portion 2*c* at a position where a desired object (living body tissue) existing in the body cavity appears in an observation visual field of the objective optical system 21*a*. Thereafter, the user operates the observation mode switching switch of the scope switch 23 to provide an instruction for setting the observation mode of the endoscope apparatus 1 to the special light observation mode.

Subsequently, a specific example of operation of each component when the observation mode of the endoscope apparatus 1 is set to the special light observation mode will be described below. Note that the following describes an example in which the wavelength band of A light emitted from the amber LED 31*d* shifts from an original wavelength band to the short wavelength side.

When having detected that an instruction for setting the observation mode of the endoscope apparatus 1 to the special light observation mode is provided, the control unit 44 generates a control signal for simultaneously emitting G light and A light from the light source apparatus 3, and outputs the generated control signal to the light source control unit 34.

In the special light observation mode, the light source control unit 34 controls the light emission unit 31, for example, not to emit light from the violet LED 31*a*, the blue LED 31*b*, and the red LED 31*e* and to simultaneously emit light from the green LED 31*c* and the amber LED 31*d* in accordance with the control signal outputted from the control unit 44. Then, in accordance with such operation of the light source control unit 34, an object is irradiated with illumination light including G light and A light, and an image-pickup signal GS generated through image pickup of the G light included in return light of the illumination light and an image-pickup signal AS generated through image pickup of the A light included in the return light are outputted from the image pickup device 21*b* to the signal processing unit 41. In other words, in the special light observation mode, the image pickup unit 21 of the present embodiment performs image pickup of return light from the object including a region containing hemoglobin illuminated with the G light and the A light, and outputs image-pickup signals.

The signal processing unit 41 performs predetermined signal processing on the image-pickup signals GS and AS sequentially outputted from the image pickup device 21*b* to generate image data PG that is image data of a green color component in accordance with signal intensity of the image-pickup signal GS and image data PA that is image data of an amber color component in accordance with signal intensity of the image-pickup signal AS, and outputs the image data PG and PA to the image processing unit 42 and the control unit 44.

The control unit 44 performs brightness detection processing for detecting present brightness SCB in the special light observation mode based on the image data of each color component outputted from the signal processing unit 41.

Specifically, in the above-described brightness detection processing, for example, the control unit 44 calculates an average value of pixel values of pixels included in the image data PG and PA outputted from the signal processing unit 41, and performs processing for detecting the calculated average value as the present brightness SCB in the special light observation mode. Note that, in the above-described brightness detection processing, the control unit 44 may perform processing for detecting, as the present brightness SCB in the special light observation mode, for example, one of a weighted average value of the pixel values of pixels included in the image data PG and PA outputted from the signal processing unit 41 or an average value of the pixel values of pixels included in the image data PA outputted from the signal processing unit 41. When performing the above-described brightness detection processing, the control unit 44 may perform the processing for an entire range of the image data outputted from the signal processing unit 41 or only for a partial region of the image data outputted from the signal processing unit 41.

The control unit 44 generates a control signal for performing light modulation operation through which the present brightness SCB obtained as a processing result of the above-described brightness detection processing becomes closer to a brightness target value STB in the special light observation mode, and outputs the generated control signal to the light source control unit 34. Specifically, the control unit 44 generates a control signal for performing, for example, light modulation operation through which a ratio (SCB/STB) of the present brightness SCB relative to the brightness target value STB becomes closer to one, and outputs the generated control signal to the light source control unit 34. Specifically, through such light modulation operation, for example, the current value of current supplied from the light source control unit 34 to the amber LED 31d becomes relatively small in short-distance observation in which observation is performed with the distal end portion 2c being positioned close to an object in a subject, and the current value of current supplied from the light source control unit 34 to the amber LED 31d becomes relatively large in long-distance observation in which observation is performed with the distal end portion 2c being positioned away from the object in the subject.

When having detected that an instruction for setting the observation mode of the endoscope apparatus 1 to the special light observation mode is provided, the control unit 44 performs operation for reading table data TD from the memory 44a. In addition, the control unit 44 having detected that the instruction for setting the observation mode of the endoscope apparatus 1 to the special light observation mode is provided detects a present value C1 of current supplied from the light source control unit 34 to the amber LED 31d of the light emission unit 31.

Figures 4, 5:
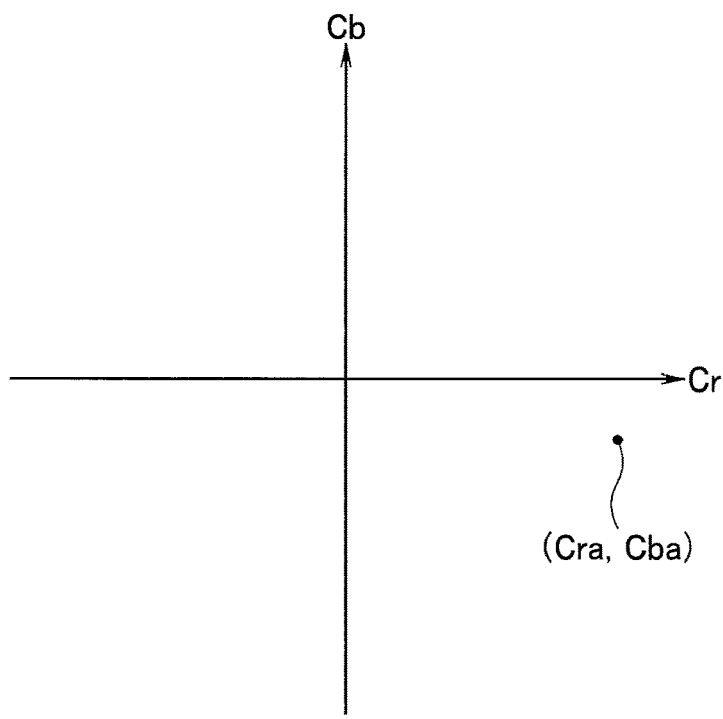
FIG. 4 is a diagram illustrating an example of table data used in processing by a processor according to the embodiment.
FIG. 5 is a diagram in which reference color differences used in processing by the processor according to the embodiment are indicated as coordinate values of an orthogonal coordinate system.

For example, as illustrated in FIG. 4, the table data TD is produced as data representing a correspondence relation between the current value CV of current supplied to the amber LED 31d and a signal output ratio SR of image-pickup signals outputted from the image pickup device 21b. FIG. 4 is a diagram illustrating an example of table data used in processing at the processor according to the embodiment.

The current value CV is set as a value appropriate for an operation aspect of light modulation operation of the amber LED 31d by the light source control unit 34. Specifically, for example, when light modulation operation of the amber LED 31d by the light source control unit 34 is performed at steps of 1 ampere in a range from 1 ampere to 10 amperes, 10 current values included in the range are set as current values CVA, CVB, CVC, . . . , CVM included in the table data TD in FIG. 4. In the table data TD in FIG. 4, the current value CVA corresponds to a lower limit value of current supplied to the amber LED 31d, and the current value CVM corresponds to an upper limit value of current supplied to the amber LED 31d.

The signal output ratio SR is set as, for example, a value obtained by generating A light having a predetermined light quantity LMT from the amber LED 31d, irradiating, with the A light, a reference object including a region containing hemoglobin (or a region having a light absorption characteristic same as a light absorption characteristic of hemoglobin) while gradually changing the central wavelength of A light from 600 nm to the short wavelength side, acquiring signal intensity SVI of the image-pickup signal AS sequentially outputted from the image pickup device 21b in accordance with the irradiation with the A light, and calculating a ratio of the acquired signal intensity SVI relative to reference signal intensity SVT (to be described later). Specifically, the signal intensity SVI is acquired as the signal intensity of the image-pickup signal AS outputted from the image pickup unit 21 when an object including a region containing hemoglobin is irradiated with A light having intensity between a wavelength band including a local maximum value and a wavelength band including a local minimum value in a light absorption characteristic of hemoglobin and having a central wavelength different from 600 nm.

In the present embodiment, the table data TD is produced based on a premise that a relation between the current value of current supplied to the amber LED 31d in accordance with light modulation operation by the light source control unit 34 and the central wavelength of A light emitted from the amber LED 31d in accordance with the light modulation operation is known. The reference signal intensity SVT is a value obtained as the signal intensity of the image-pickup signal AS outputted from the image pickup device 21b when the above-described reference object is irradiated with A light having the predetermined light quantity LMT and a central wavelength set to be 600 nm.

Thus, in the table data TD in FIG. 4, the signal output ratio SR corresponding to an upper limit value of the light modulation operation by the light source control unit 34 and corresponding to the current value CVM with which the central wavelength of A light emitted from the amber LED 31d is 600 nm is set to be 1.0. The table data TD in FIG. 4 indicates a correspondence relation among the current values CVA, CVB, CVC, . . . with which the central wavelength of A light belonging to a range of the light modulation operation by the light source control unit 34 and emitted from the amber LED 31d is shorter than 600 nm, and signal output ratios SRA, SRB, SRC, . . . acquired as a value larger than zero and smaller than 1.0.

Note that, according to the present embodiment, for example, data representing a correspondence relation between a temperature TV of the amber LED 31d and the signal output ratio SR of the image-pickup signal AS outputted from the image pickup device 21b may be stored in the memory 44a as the table data TD in place of the above-described data. In such a case, the control unit 44 may detect a present temperature CT of the amber LED 31d, specify, based on the table data TD, the temperature TV corresponding to the detected present temperature CT, acquire the signal output ratio SR associated with the specified temperature TV, and output a control signal including the acquired signal Output ratio SR to the color adjustment processing unit 42a and the color correction processing unit 42b. In addition, according to the present embodiment, for example, the light source apparatus 3 may be provided with a spectroscopic detector capable of detecting a present central wavelength WP of A light emitted from the amber LET) 31d, and the signal output ratio SR in accordance with a result of detection by the spectroscopic detector may be acquired by the control unit 44. In addition, according to the present embodiment, for example, a plurality of pieces of table data TD produced for respective individual identification numbers of the amber LED 31d may be stored in the memory 44a.

The control unit 44 specifies, with reference to the table data TD read from the memory 44a, the current value CV corresponding to the present value CI of current supplied from the light source control unit 34 to the amber LED 31d of the light emission unit 31, acquires the signal output ratio SR associated with the specified current value CV, and outputs a control signal including the acquired signal output ratio SR to the color adjustment processing unit 42a and the color correction processing unit 42b.

Specifically, the control unit 44 of the present embodiment acquires, with reference to the table data TD based on a detection result obtained by detecting the present current value CI corresponding to a parameter indicating a present operation state of the amber LED 31d as a generation source of A light in the light emission unit 31, signal intensity information related to the signal intensity of the image-pickup signal AS outputted from the image pickup unit 21 in accordance with irradiation of an object including a region containing hemoglobin with A light. The control unit 44 of the present embodiment acquires, as the signal intensity information, the signal output ratio SR calculated as the ratio of the signal intensity SVI relative to the reference signal intensity SVT. The control unit 44 of the present embodiment performs operation of outputting a control signal including the signal output ratio SR to the color adjustment processing unit 42a and the color correction processing unit 42b, as operation corresponding to control for maintaining, at a constant ratio, a brightness ratio of image data used to generate an observation image by the observation image generation unit 43, based on the signal intensity information. Note that the control unit 44 of the present embodiment may obtain a detection result by detecting the present temperature CT of the amber LED 31d as the parameter indicating the present operation state of the amber LED 31d. The control unit 44 of the present embodiment may obtain a detection result by detecting the present central wavelength WP of the amber LED 31d as the parameter indicating the present operation state of the amber LED 31d. The control unit 44 of the present embodiment may acquire the signal intensity information (signal output ratio SR) in accordance with an individual identification number of the amber LED 31d.

In the special light observation mode, the color adjustment processing unit 42a performs, in accordance with the control signal outputted from the control unit 44, color adjustment processing on the image data PG outputted from the signal processing unit 41. Specifically, the color adjustment processing unit 42a performs, as the color adjustment processing, processing of multiplying the pixel value of each pixel in the image data PG by the signal output ratio SR included in the control signal outputted from the control unit 44. Specifically, through such color adjustment processing, image data SPG obtained by multiplying the pixel value of each pixel in the image data PG by the signal output ratio SR, and the image data PA are outputted from the color adjustment processing unit 42a to the color correction processing unit 42b.

Note that, according to the present embodiment, for example, processing of multiplying the pixel value of each pixel in the image data PA by a reciprocal of the signal output ratio SR may be performed at the color adjustment processing unit 42a. When such processing is performed at the color adjustment processing unit 42a, the image data PG and image data IPA obtained by multiplying the pixel value of each pixel in the image data PA by the reciprocal of the signal output ratio SR are outputted to the color correction processing unit 42b.

According to the present embodiment, the color adjustment processing unit 42a may perform, as the color adjustment processing, one of processing fir obtaining the image data SPG or processing for obtaining the image data IPA. Specifically, the color adjustment processing unit 42a of the present embodiment performs, as the color adjustment processing based on the signal output ratio SR obtained in accordance with control by the control unit 44, one of processing for adjusting brightness of the image data PA or processing for adjusting brightness of the image data PG.

The color correction processing unit 42b performs processing for calculating color differences Cr and Cb for each pixel based on the image data SPG and PA outputted from the color adjustment processing unit 42a. The color correction processing unit 42b also performs processing for acquiring the signal output ratio SR included in the control signal outputted from the control unit 44.

Note that values of the color differences Cr and Cb calculated by the color correction processing unit 42b of the present embodiment can be obtained by applying pixel values in the image data SPG to a B (blue) component and a G (green) component of a well-known conversion equation and applying pixel values in the image data PA to a R (red) component of the conversion equation.

The color correction processing unit 42b extracts, from among the image data of the color components outputted from the color adjustment processing unit 42a, a target region AP corresponding to a group of pixels for which the values of the color differences Cr and Cb are both negative values. In addition, the color correction processing unit 42b performs processing using Equation (1) described below to set, for each pixel included in the target region AP in the image data SPG, a color correction coefficient Tp in accordance with the color differences Cr and Cb calculated as described above. Note that, in Equation (1) described below, Fa and Fb represent predetermined constants, Cra and Cba represent values of reference color differences set in accordance with a reference color of a living body, and Crt and Cbt represent values of color differences calculated for a target pixel included in the target region AP. In addition, in Equation (1) described below, |Crt−Cm| represents an absolute value of a value obtained by subtracting the reference color difference Cra from the color difference Crt, and |Cbt−Cba| represents an absolute value of a value obtained by subtracting the reference color difference Cba from the color difference Cbt.

$$Tp=(1+Fa\times|Crt-Cra|)\times(1+Fb\times|Cbt-Cba|) \qquad (1)$$

Specifically, the color correction coefficient Tp is set as a value that monotonically increases as a color of the target pixel included in the target region AP in the image data SPG is further separated from the reference color of the living body.

Note that, according to the present embodiment, the reference color differences Cra and Cba can be set as, for example, values plotted as coordinate values in a fourth quadrant of a Cr–Cb coordinate system that is an orthogonal coordinate system having the color difference Cr on a horizontal axis and the color difference Cb on a vertical axis (refer to FIG. 5). Specifically, according to the present embodiment, the value of the reference color difference Cra can be set to increase from zero, and the value of the reference color difference Cba can be set to decrease from zero. FIG. 5 is a diagram in which reference color differences used in processing at the processor according to the embodiment are indicated as coordinate values of an orthogonal coordinate system.

According to the present embodiment, for example, when data representing a correspondence relation between the current value CV and each of the values of the reference color differences Cra and MI is included in the table data TD, the control unit 44 may perform control to change the values of the reference color differences Cra and Cha in accordance with a detection result of the present value CI of current supplied to the amber LED 31d.

The color correction processing unit 42b corrects the pixel value of each pixel included in the target region AP in the image data SPG by applying the signal output ratio SR and the color correction coefficient Tp to Equation (2) described below and performing calculation. Note that, in Equation (2) described below, Pa represents a pixel value of a target pixel included in the target region AP in the image data SPG before correction, and Pb represents a pixel value of the target pixel after correction.

$$Pb = Pa \times [1 - Tp + (Tp/SR)] \quad (2)$$

Specifically, according to Equation (2) described above, color correction processing for decreasing saturation of a region not containing hemoglobin in the image data SPG is performed at the color correction processing unit 42b based on the signal output ratio SR obtained in accordance with control by the control unit 44 and the color differences Cr and Cb calculated by using the image data SPG and PA obtained as a processing result of the color adjustment processing by the color adjustment processing unit 42a. Then, when the processing using Equation (2) described above is performed at the color correction processing unit 42b, image data SCPG obtained by performing the color correction processing on each pixel included in the target region AP in the image data SPG, and the image data PA are outputted from the color correction processing unit 42b to the observation image generation unit 43.

The color correction processing unit 42b of the present embodiment may perform, for example, processing of correcting the pixel value of each pixel included in the target region AP in the image data PA by using Equation (3) described below. Note that, in Equation (3) described below, Pc represents a pixel value of a target pixel included in the target region AP in the image data PA before correction, and Pd represents a pixel value of the target pixel after correction.

$$Pd = Pc \times (1 - Tp + SR \times Tp) \quad (3)$$

Specifically, according to Equation (3) described above, the color correction processing for decreasing saturation of a region not containing hemoglobin in the image data PA is performed at the color correction processing unit 42b based on the signal output ratio SR obtained in accordance with control by the control unit 44 and the color differences Cr and Cb calculated by using the image data SPG and PA obtained as a processing result of the color adjustment processing by the color adjustment processing unit 42a. When the processing using Equation (3) described above is performed at the color correction processing unit 42b, the image data SPG and image data CPA obtained by performing the color correction processing on each pixel included in the target region AP in the image data PA are outputted to the observation image generation unit 43.

According to the present embodiment, the color correction processing unit 42b may perform, as the color correction processing, one of the processing using Equation (2) described above or the processing using Equation (3) described above.

In the special light observation mode, the observation image generation unit 43 generates, in accordance with the control signal outputted from the control unit 44, a special light observation image by, for example, allocating the image data SCPG outputted through the color correction processing unit 42b to the B and G channels of the display apparatus 5 and allocating the image data PA outputted through the color correction processing unit 42b to the R channel of the display apparatus 5, and outputs the generated special light observation image to the display apparatus 5.

In a wavelength band near 600 nm, which is the original central wavelength of A light emitted from the amber LED 31d, an absorptivity of hemoglobin steeply increases as a wavelength of illumination light shifts to the short wavelength side. The central wavelength of A light emitted from the amber LED 31d shifts to a wavelength shorter than 600 nm along with, for example, decrease of the value of current supplied from the light source control unit 34 to the amber LED 31d.

Thus, for example, when light modulation operation through which a ratio of the present brightness SCB relative to the brightness target value STB becomes closer to one is simply performed, the wavelength band of A light shifts from the original wavelength band to the short wavelength side along with decrease of the value of current supplied to the amber LED 31d in short-distance observation, and a light quantity of return light of A light subjected to image pickup by the image pickup device 21b decreases along with increase of an absorption amount of A light in a region containing hemoglobin, such as a blood vessel and blood. In other words, when the above-described light modulation operation is simply performed in the special light observation mode, such a phenomenon that a color tone of a region containing hemoglobin in an observation image displayed on the display apparatus 5 is largely different between short-distance observation and long-distance observation can occur.

However, according to the present embodiment, one of processing for acquiring, with reference to the table data TD, the signal output ratio SR in accordance with the detection result of the present value CI of current supplied to the amber LED 31d and for decreasing the brightness of the image data PG and PR in accordance with the acquired signal output ratio SR, or processing for increasing the brightness of the image data PA in accordance with the acquired signal output ratio SR is performed. In addition, according to the present embodiment, one of the processing using Equation (2) described above or the processing using Equation (3) described above is performed on each pixel included in the above-described target region AP.

Thus, according to the present embodiment, in the special light observation mode, the color tone of a region containing hemoglobin, such as a blood vessel and blood in an observation image displayed on the display apparatus 5 can be maintained at a constant color tone even when light modulation operation in accordance with an observation distance from the object is performed. In addition, according to the present embodiment, in the special light observation mode, the color tone of a region not containing hemoglobin, such as a connective tissue and a treatment instrument in an observation image displayed on the display apparatus 5 can be maintained at a constant color tone even when light modulation operation in accordance with the observation distance from the object is performed. Thus, according to the present embodiment, for example, it is possible to reduce a load on a user who performs treatment on a desired site in a living body while observing a deep blood vessel existing at a deep part of a living body tissue at the desired site.

Note that, according to the present embodiment, for example, when the observation mode of the endoscope apparatus 1 is set to the special light observation mode, the control unit 44 may perform operation that generates a control signal for sequentially (alternately) emitting G light and A light from the light source apparatus 3 and outputs the generated control signal to the light source control unit 34.

Then, through the above-described operation by the control unit 44, when the observation mode of the endoscope apparatus 1 is set to the special light observation mode, control not to emit light from the LEDs other than the amber LED 31d and to emit light from the amber LED 31d and control not to emit light from the LEDs other than the green LED 31c and to emit light from the green LED 31c are alternately and repeatedly performed by the light source control unit 34, and an object is sequentially (alternately) irradiated with G light and A light as illumination light. In addition, through the above-described operation by the control unit 44, when the observation mode of the endoscope apparatus 1 is set to the special light observation mode, the image-pickup signal GS generated through image pickup of return light from the object irradiated with G light and the image-pickup signal AS generated through image pickup of return light from the object irradiated with A light are sequentially outputted from the image pickup device 21b, and the image data PG in accordance with the signal intensity of the image-pickup signal GS and the image data PA in accordance with the signal intensity of the image-pickup signal AS are generated by the signal processing unit 41.

According to the present embodiment, for example, an object may be irradiated with B light in place of G light in the special light observation mode. In such a case, for example, when the observation mode of the endoscope apparatus 1 is set to the special light observation mode, the image data PB is acquired in place of the image data PG, and the color adjustment processing by the color adjustment processing unit 42a and the color correction processing by the color correction processing unit 42b are sequentially performed on the image data PB.

According to the present embodiment, for example, in the special light observation mode, the control unit 44 may perform control for adjusting a gain of the image-pickup signal AS based on the signal output ratio SR, in place of the color adjustment processing based on the signal output ratio SR by the color adjustment processing unit 42a. Specifically, for example, in the special light observation mode, the control unit 44 may perform, on the image pickup device 21b, control for setting a gain of the image-pickup signal GS to be GP and setting a gain GQ of the image-pickup signal AS to be (1/SR) times as large as the gain GP.

According to the present embodiment, for example, in the special light observation mode, the control unit 44 may perform control for adjusting a light quantity of A light emitted from the light emission unit 31 based on the signal output ratio SR, in place of the color adjustment processing based on the signal output ratio SR by the color adjustment processing unit 42a. Specifically, for example, in the special light observation mode, the control unit 44 may perform, on the light source control unit 34, control for setting a light quantity of G light emitted from the light emission unit 31 to be LMP and setting a light quantity LMQ of A light emitted from the light emission unit 31 to be (1/SR) times as large as the light quantity LMP. Note that, in such a case, one of a light emission time of the amber LED 31d or the value of current supplied from the light source control unit 34 to the amber LED 31d may be changed. However, when the value of current supplied from the light source control unit 34 to the amber LED 31d is changed to set the light quantity of A light to be (1/SR) times as large as the light quantity of G light, it is needed to consider that, for example, the value of current and the signal output ratio SR change in conjunction with each other as indicated in Equation (4) described below. Note that Equation (4) described below expresses an example in which the value of current supplied to the amber LED 31d is changed from a present current value Ic (equivalent to the above-described current value CD to a new current value In. In Equation (4) described below, SRIc represents a signal output ratio corresponding to the current value Ic in the table data TD, and SRIn represents a signal output ratio corresponding to the current value In in the table data TD.

$$1/SRIc = (In \times SRIn)/(Ic \times SRIc) \qquad (4)$$

Equation (4) described above can be rewritten as Equation (5) described below.

$$0 = In \times SRIn - Ic \qquad (5)$$

For example, when it is assumed that the signal output ratio SR in the table data ID is approximated to a linear function of the current value CV, Equation (5) described above can be expressed as a quadratic equation of the current value In. In the special light observation mode, through control for supplying current of the current value In (>0) obtained as a solution of the above-described quadratic equation to the amber LED 31d, it is possible to set the light quantity of A light to be (1/SR) times as large as the light quantity of G light and set the ratio of the present brightness SCB relative to the brightness target value SIB to be closer to one.

In the present embodiment, for example, the light source apparatus 3 may include a white light source such as a xenon lamp and a plurality of optical filters each having an optical property that allows transmission of light of five colors, namely. V light, B light, G light. A light, and R light, and may be configured to be able to sequentially generate the light of five colors. In addition, in the present embodiment, for example, the image pickup device 21b may be configured as a monochrome image sensor including no color filter 21f on the image pickup surface when the light source apparatus 3 is configured to be able to sequentially generate the above-described light of five colors.

Note that the present invention is not limited to the above-described embodiment but may be subjected to various kinds of modifications and applications without departing from the scope of the invention.

What is claimed is:

1. An endoscope apparatus comprising:
   a light source apparatus configured to sequentially or simultaneously generate first light and second light, wherein a wavelength band of the first light belongs to a red color gamut, and a wavelength band of the second light being out of the wavelength band of the first light and having a shorter wavelength than the first light;
   an image pickup apparatus configured to generate a first image-pickup signal of a first image based on return light from an object irradiated with the first light, and generate a second image-pickup signal of a second image based on the return light from the object irradiated with the second light; and a processor configured to:
acquire signal intensity information based on a predetermined parameter indicating a present operation state of the light source apparatus,
wherein the signal intensity information is a ratio of (i) signal intensity of the first image-pickup signal when the object is irradiated with the first light having a central wavelength different from a predetermined central wavelength of the first light having the wavelength band belonging to the red color gamut, with respect to (ii) reference signal intensity of the image-pickup signal when the object is irradiated with the first light having the wavelength belonging to the red color gamut; and
perform, based on the signal intensity information, control of the light source apparatus to maintain a brightness ratio of the first image and the second image at a constant ratio.

2. The endoscope apparatus according to claim 1, further comprising:
a color filter comprising a first filter and a second filter,
the first filter having an optical property that allows transmission of the first light,
the second filter having an optical property that allows transmission of the second light,
wherein the image pickup apparatus is configured to:
generate the first image-pickup signal by performing image pickup of the first light that is included in the return light from the object irradiated with illumination light including the first light and the second light and passed through the first filter; and
generate the second image-pickup signal by performing image pickup of the second light that is included in the return light from the object irradiated with the illumination light including the first light and the second light and passed through the second filter.

3. The endoscope apparatus according to claim 1,
wherein the processor is configured to generate an observation image by allocating the first image to a red channel of a display apparatus and by allocating the second image to a blue channel and a green channel of the display apparatus.

4. The endoscope apparatus according to claim 1,
wherein the wavelength band of the first light is set to not overlap the wavelength band of the second light, and
wherein a central wavelength of the first light is set to be a wavelength belonging to a range of 585 nm to 615 nm, inclusive.

5. The endoscope apparatus according to claim 1,
wherein the wavelength band of the second light is set to not overlap the wavelength band of the first light, and
wherein a central wavelength of the second light is set to be a wavelength belonging to a range equal to or longer than 400 nm and shorter than 585 nm.

6. The endoscope apparatus according to claim 1,
wherein the processor is configured to:
adjust brightness of a processing target image corresponding to one of the first or second images based on the acquired signal intensity information and two color differences calculated by using the first and second images;
perform color adjustment processing for decreasing saturation of a region not containing hemoglobin in the processing target image; and
generate an observation image by using the first and second images subjected to the color adjustment processing.

7. The endoscope apparatus according to claim 6,
wherein the processor is configured to perform control for adjusting light quantity of the first light emitted from the light source apparatus based on the signal intensity information.

8. The endoscope apparatus according to claim 7,
wherein the processor is configured to adjust the light quantity of the first light emitted from the light source apparatus by changing one of a light emission time of the predetermined light source or a value of current supplied to the light source apparatus.

9. The endoscope apparatus according to claim 8,
wherein the processor is configured to perform control for adjusting a gain of the first image-pickup signal based on the signal intensity information.

10. An endoscope image processing apparatus comprising:
a processor configured to:
acquire signal intensity information based on a predetermined parameter indicating a present operation state,
wherein the signal intensity information is a ratio of (i) signal intensity of a first image-pickup signal of a first image, the first image-pickup signal being generated based on return light from an object irradiated with a first light having a central wavelength different from a predetermined central wavelength of a first light having a wavelength band belonging to a red color gamut, with respect to (ii) reference signal intensity of the first image-pickup signal when the object is irradiated with the first light having a wavelength belonging to the red color gamut; and
perform, based on the signal intensity information, control to maintain a brightness ratio of the first image and a second image at a constant ratio, the second image being picked up based on return light from the object irradiated with a second light, a wavelength band of the second light being out of the wavelength band of the first light and having a shorter wavelength than the first light.

11. The endoscope apparatus according to claim 10,
wherein the processor is configured to generate an observation image by allocating the first image to a red channel of a display apparatus and by allocating the second image to a blue channel and a green channel of the display apparatus.

12. The endoscope apparatus according to claim 10,
wherein the wavelength band of the first light is set to not overlap the wavelength band of the second light, and
wherein a central wavelength of the first light is set to be a wavelength belonging to a range of 585 nm to 615 nm, inclusive.

13. The endoscope apparatus according to claim 10,
wherein the wavelength band of the second light is set to not overlap the wavelength band of the first light, and
wherein a central wavelength of the second light is set to be a wavelength belonging to a range equal to or longer than 400 nm and shorter than 585 nm.

14. The endoscope apparatus according to claim 10,
wherein the processor is configured to:
adjust brightness of a processing target image corresponding to one of the first or second images based on the acquired signal intensity information and two color differences calculated by using the first and second images;

perform color adjustment processing for decreasing saturation of a region not containing hemoglobin in the processing target image; and generate an observation image by using the first and second images subjected to the color adjustment processing.

15. The endoscope apparatus according to claim 14, wherein the processor is configured to perform control for adjusting light quantity of the first light emitted based on the signal intensity information.

16. The endoscope apparatus according to claim 15, wherein the processor is configured to adjust the light quantity of the first light emitted from the light source apparatus by changing one of a light emission time of the predetermined light source or a value of current supplied to the light source apparatus.

17. The endoscope apparatus according to claim 16, wherein the processor is configured to perform control for adjusting a gain of the first image-pickup signal based on the signal intensity information.

18. A method for controlling an endoscope apparatus including a light source apparatus and an image pickup apparatus, the light source apparatus being configured to sequentially or simultaneously generate first light and second light, wherein a wavelength band of the first light belongs to a red color gamut, and a wavelength band of the second light being out of the wavelength band of the first light and having a shorter wavelength than the first light, and the image pickup apparatus being configured to generate a first image-pickup signal of a first image based on return light from an object irradiated with the first light, and generate a second image-pickup signal of a second image based on the return light from the object irradiated with the second light, the method comprising:

acquiring signal intensity information based on a predetermined parameter indicating a present operation state of the light source apparatus,
wherein the signal intensity information is a ratio of (i) signal intensity of the first image-pickup signal when the object is irradiated with the first light having a central wavelength different from a predetermined central wavelength of the first light having the wavelength band belonging to the red color gamut, with respect to (ii) reference signal intensity of the image-pickup signal when the object is irradiated with the first light having the wavelength belonging to the red color gamut; and performing, based on the signal intensity information, control of the light source apparatus to maintain a brightness ratio of the first image and the second image at a constant ratio.

19. A non-transitory computer-readable recording medium storing a program used in an endoscope apparatus including a light source apparatus, an image pickup apparatus, and a processor, the light source apparatus being configured to sequentially or simultaneously generate first light and second light, wherein a wavelength band of the first light belongs to a red color gamut, and a wavelength band of the second light being out of the wavelength band of the first light and having a shorter wavelength than the first light, and the image pickup apparatus being configured to generate a first image-pickup signal of a first image based on return light from an object irradiated with the first light, and generate a second image-pickup signal of a second image based on the return light from the object irradiated with the second light, wherein the program causes the processor to at least perform:

acquiring signal intensity information based on a predetermined parameter indicating a present operation state of the light source apparatus,
wherein the signal intensity information is a ratio of (i) signal intensity of the first image-pickup signal when the object is irradiated with the first light having a central wavelength different from a predetermined central wavelength of the first light having the wavelength band belonging to the red color gamut, with respect to (ii) reference signal intensity of the image-pickup signal when the object is irradiated with the first light having the wavelength belonging to the red color gamut; and performing, based on the signal intensity information, control of the light source apparatus to maintain a brightness ratio of the first image and the second image at a constant ratio.

* * * * *